United States Patent [19]
Oxenkrug et al.

[11] Patent Number: 6,063,805
[45] Date of Patent: May 16, 2000

[54] METHOD FOR TREATING HYPERTENSION

[75] Inventors: Gregory F. Oxenkrug, Newton, Mass.; Pura J. Requintina, West Kingston, R.I.

[73] Assignee: St. Elizabeth's Medical Center of Boston, Boston, Mass.

[21] Appl. No.: 09/185,562

[22] Filed: Nov. 4, 1998

Related U.S. Application Data

[63] Continuation of application No. PCT/US98/04909, Mar. 12, 1998.
[60] Provisional application No. 60/042,665, Apr. 4, 1997.
[51] Int. Cl.⁷ .......................... A01N 43/38; A61K 31/40; A61K 31/405
[52] U.S. Cl. .......................... 514/415; 514/46; 514/416; 514/419
[58] Field of Search .............................. 514/46, 415, 416, 514/419

[56] References Cited

U.S. PATENT DOCUMENTS 4,600,723   7/1986   Short et al. .............................. 514/416

OTHER PUBLICATIONS

Chemical Abstract 96:15483, "Hypotensive Effect of Melatonin in Essential Hypertension" Oct. 1981.

Database CA on STN, Assession No. 106:27721, Oxenkrug, et al., Sch. Med. Wayne State University, Abstract to *J. Neural Transm* 1986, vol. 66, No. 3–4, pp. 271–281.

*Primary Examiner*—Frederick Krass
*Attorney, Agent, or Firm*—Nixon Peabody LLP

[57] ABSTRACT

The present invention relates to a method of treatment of hypertension in a mammal, particularly a human being. This method comprises the administration of a therapeutically effective hypertension treatment amount of N-acetylserotonin (NAS) to the mammal.

6 Claims, No Drawings

METHOD FOR TREATING HYPERTENSION

This application claims the benefit of U.S. Provisional Application Ser. No. 60/042,665, filed Apr. 4, 1997, and is a continuation of PCT/US98/04909, filed Mar. 12, 1998.

BACKGROUND OF THE INVENTION

1. Field of the Invention

The present invention relates to a method of treatment of hypertension in a mammal, particularly a human being. This method comprises the administration of a therapeutically effective hypertension treatment amount of N-acetylserotonin (NAS) to the mammal.

2. Background

Hypertension may be defined as a condition of sustained elevated arterial blood pressure, i.e., a diastolic pressure in excess of 90 mm Hg. In the majority of cases, the patients are affected by essential hypertension, which by definition means that the underlying etiologic mechanism(s) is unknown. Regardless of the mechanism, a sustained elevation of blood pressure for a period of time has been shown to result in significant cardiovascular damage throughout the body, e.g., congestive heart failure, coronary artery disease, stroke and progressive renal failure [Veterans Administration Cooperative Study Group on Antihypertensive Agents: Effects of Treatment on Morbidity in Hypertension. Results in patients with diastolic blood pressures averaging 115 through 129 mm Hg, J.A.M.A., (1967), 202, 1028 and Veterans Administration Cooperative Study Group on Antihypertensive Agents: Effects of Treatment on Morbidity in Hypertension II.Results in patients with diastolic blood pressures averaging 90 through 114 mm Hg, J.A.M.A., (1970), 213, 1143].

The benefits of drug therapy to reduce and control blood pressure have been established [Woods, J. W., Current Therapy, ed. Conn, H. F., pp. 219–220, 1981]. Since the specific etiology is not usually known, an empirical approach to the treatment of hypertensive patients is taken. Often, the choice of treatment is based on the severity of the disease and the patient's response and compliance to initial therapy. The goal of the treatment is to reduce elevated blood pressure and maintain pressure at or near normal levels.

The effect of the pineal gland extracts on the blood pressure has been first described as without any influence in some experiments and a marked fall in blood pressure in the other experiments (Howell, 1898). This inconsistency continued to be reported by the consequent studies in the beginning of the 20th century (see for rev., Horrax, 1916). Most recently, the possible hypotensive effect of the pineal gland was suggested by the finding that surgical pinealectomy induced moderate and transient hypertension in normotensive SpragueDawley rats (Zanoboni & Zanoboni-Muciaccia, 1967; see Karppanen, 1974). This suggestion was further supported by the observation of the hypotensive effect of the selective inhibitors of monoamine oxidase A type (MAO-A) which also stimulate pineal melatonin biosynthesis (Oxenkrug et al., 1984; see for rev., Oxenkrug, 1991). Furthermore, surgical pinealectomy attenuated the hypotensive effect of clorgyline, a selective monoamine oxidase-A inhibitor (Oxenkrug et al., 1986). Some authors have suggested that hypertension in pinealectomized Wistar rats depended rather on the changed reactivity to stressful stimuli than on the pineal gland deficiency (Holmes & Sugden, 1975).

In contrast to the suggested hypotensive effect of the pineal gland observed in normotensive rats, the hyperfunction of the pineal gland was reported in the spontaneously hypertensive rats (SHR), the most recognized animal model of human essential hypertension (Finocchiaro et al., 1990; Illnerova & Albrecht, 1975; Kawashima et al. 1984). In addition, surgical or chemical pinealectomy (administration of sympathetic nerve's toxin, 6-OHDA-Reuss & Oxenkrug, 1989) prevented or attenuated the development of hypertension in SHR rats (Haeusler et al., 1972) and blocked the elevation of blood pressure in episodic hypoxia (Fletcher et al., 1992).

DETAILED DESCRIPTION OF THE INVENTION

The previous studies assessed the function of the pineal gland in SHR rats by measuring the pineal NAT activity and/or pineal and blood levels of melatonin with the use of radioassavs which could not detect NAS levels (see Kawasima et al., 1984). HPLC-fluorimetric method which allows for the simultaneous determination of NAS, melatonin, serotonin and 5-hydroxyindole acetic acid (5-HLAA) in the single pineal gland have been applied (see Oxenkrug et al., 1986).

We have found pineal NAS (but not melatonin) levels higher in normotensive (4 week old) SHR rats than in hypertensive (12-week old) SHR rats while there was no differences in the pineal NAS production between 4- and 12-week old WKY rats. (SHR rats are born with the normal blood pressure and develop hypertension only by the 12–14 weeks of age, see Okamoto & Aoki, 1963). In addition, the circadian rhythm of the pineal NAS and melatonin was phase-advanced in 12 week old SHR (hypertensive) rats in comparison with the 12 week old normotensive WKY rats (Oxenkrug and Requintina, 1991). The differences in the pineal NAS production between SHR and WKY rats became even more obvious when we studied the pineal NAS response to the selective MAO-A inhibitor, clorgyline, and to cold-immobilization stress (which elevates the production of the endogenous MAO inhibitor, tribulin) (Bhattacharya et al., 1988). Both clorgyline and cold-immobilization stress induced higher pineal levels of NAS in SHR than in WKY rats (Oxenkrug & Requintina, 1997) and normotensive rats of Sprague-Dawley and Fisher 344N strain (see Oxenkrug, 1991). Our data is in agreement with the finding of Illnerova & Albrecht (1975) showing the higher stimulation of the NAT activity by isopreterenol in SHR than in WKY rats. However, contrary to the traditional interpretation of their data as an the evidence of melatonin hyperproduction in SHR rats, we found that NAS hyperproduction was not accompanied by the higher melatonin levels in response to cold-immobilization stress.

Based on these findings we suggested that the hyperproduction of NAS (but not melatonin) is the specific feature of SHR rats which protects against the development of hypertension in young SHR rats, and that the decline of the pineal NAS production by the 12 weeks of age facilitates the development of hypertension in SHR rats. To check our hypothesis that NAS might have hypotensive effect we have studied the NAS effect on blood pressure in hypertensive SHR rats and have found that NAS exerts a hypotensive effect.

The present invention relates to a method of treatment of hypertension in a mammal, preferably a human being. This method comprises the administration of a therapeutically effective hypertension treatment amount of N-acetylserotonin (NAS), also referred to as N-acetyl-5-hydroxytryptamine, or a pharmaceutically acceptable salt thereof, to the mammal. The NAS may be administered alone or in combination with other agents.

The effective antihypertensive amount of NAS required for use in the above conditions will vary both with the route of administration, the condition under treatment and the mammal undergoing treatment, and is ultimately at the discretion of the physician. A suitable oral dose of the active compound for a mammal is in the range of from about 0.01 to about 500 mg per kilogram body weight per day; preferably from about 0.1 to about 40 mg/kg and optimally about 7 mg per kg of human bodyweight per day, although the precise dosage will naturally depend on a number of clinical factors, for example, the age of the recipient, the route of administration and the condition under treatment and its severity: for administration of NAS by the oral route, a dosage regime of 0.03 to 30 mg per kg per day, preferably 1 to 20 mg per kg per day and optimally about 7 mg per kg per day, may be used. The desired daily dose is preferably given as two or three or more subdoses administered at appropriate intervals during the day.

While it is possible for the active compound to be administered alone as the raw chemical, it is preferable to present the active compound as a pharmaceutical formulation. Formulations of the present invention, both for veterinary and for human medical use, comprise the active compound together with one or more pharmaceutically acceptable carriers therefor and optionally any other therapeutic ingredients. The carrier(s) must be pharmaceutically acceptable in the sense of being compatible with the other ingredients of the formulation and not deleterious to the recipient.

The formulations include those suitable for oral, transdermal, rectal or parenteral (including subcutaneous, intramuscular and intravenous) administration. Formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier, or both, and then, if necessary, shaping the product into the desired formulation.

Formulations of the present invention suitable for oral administration may be presented as discrete units such as capsules, cachets, tablets or lozenges, each containing a predetermined amount of the active compound; as a powder or granules; or as a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, the active compound being in a free-flowing form such as a powder or granules, optionally mixed with a binder, disintegrants, lubricant, inert diluent, or surface active/dispersing agent. Molded tablets, comprising a mixture of the powdered active compound with any suitable carrier, may be made by molding in a suitable machine. The tablets may optionally be coated or scored and may be formulated so as to provide slow or controlled release of the active ingredient therein. The tablets may optionally be provided with an enteric coating to release in parts of the gut other than the stomach.

A syrup may be made by adding the active compound to a concentrated, aqueous solution of a sugar; for example, sucrose, to which may also be added any accessory ingredient(s). Such accessory ingredient(s) may include flavorings, an agent to retard crystallization of the sugar or an agent to increase the solubility of any other ingredient, such as a polyhydric alcohol, for example, glycerol or sorbitol, and suitable preservatives.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

When used in medicine, the salts of NAS should be pharmaceutically acceptable acid addition salts, but pharmaceutically unacceptable salts may conveniently be used to prepare the base or pharmaceutically acceptable salts of the base, and are not excluded from the scope of this invention. Suitable pharmaceutically acceptable salts include, but are not limited to, those prepared from the following acids: hydrochloric, hydrobromic, hydroiodic, sulfuric, nitric, phosphoric, maleic, salicylic, p-toluenesulfonic, tartaric, citric, acetic, methanesulfonic, formic, succinic, naphthalene-2-sulfonic, isethionic, lactobionic and benzenesulfonic.

NAS may be prepared by those methods known in the art or purchased commercially from, for example, Sigma Chemical Company.

NAS may be administered alone or in combination with other therapeutically effective agents including, for example, clinically acceptable anti-hypertensive agents.

Inhibitors of NAS conversion into melatonin, e.g., S-adenosylhomocysteine (SAM), may also be administered along with NAS to keep NAS levels at desirable levels.

The present invention is further illustrated by the following Examples. These Examples are provided to aid in the understanding of the invention and are not construed as a limitation thereof.

EXAMPLE

Methods

Hypertensive (12 week old) SHR rats (male, Charles River) were used in the study. Since systemically administered NAS is rapidly converted into melatonin (Oxenkrug & Requintina, 1995), we have studied NAS effect on blood pressure in pinealectomized and sham-operated SHR rats and in rats pretreated with the S-adenosyihomocystein (SAH), the inhibitor of the NAS conversion into melatonin. Blood pressure was measured by the indirect, non-invasive tail-cuff method (Bunag and Butterfield, 1982) (with the equipment purchased from IITC, Inc., Woodland Hills, Calif.). Rats were kept at 12 hrs light: 12 hrs dark schedule with the free access to water and food for, at least, two weeks before the experiments. Both groups consisted of 6 animals. SAH (30 mg/kg, i.p.) was injected 30 mm before NAS (30 mg/kg, s.c.). Blood pressure was evaluated 30 mm after NAS injection. Results were expressed as means±s.e. The differences between the groups were analyzed by one-way ANOVA a Student t-test.

Results

NAS induced moderate (−12%) decrease of blood pressure in the sham-operated SHR rats. The hypotensive effect of NAS was more pronounced in the pinealectomized rats (–18%). Blood pressure after NAS administration was lower in pinealectomized rats (–11%) than in sham-operated animals.

Combination of NAS and SAH decreased blood pressure in both sham-operated (–25%) and pinealectomized (–18%) rats. However, pretreatment with SAH augmented hypotensive effect of NAS only in sham-operated rats (–25% vs –12%) but not in pinealectomized (–18% in both groups) rats. There was no statistically significant differences in hypotensive effect of NAS in SAH-pretreated sham-operated and pinealectomized rats (5%) (Table 1).

TABLE 1

The NAS effect on blood pressure in spontaneously hypertensive rats

| NAS | | SAH + NAS | |
|---|---|---|---|
| BP before | BP after | BP before | BP after |
| Sham Operated SHR's | | | |
| 221 ± 21.25** | 195 ± 19.79● | 211.67 ± 12.13* | 158.33 ± 6.87 |
| Pinealectomized SHR's | | | |
| 210 ± 11.55* | 174 ± 9.17# | 205 ± 18.03* | 167.33 ± 5.73# |

BP - systolic blood pressure (mmHg), mean + S.E.
*p < 0.0001,
**p < 0.04 vs. BP after the treatment
p < 0.03 vs. corresponding sham operated group
●p < 0.001 vs. corresponding SAH + NAS group Discussion To the best of our knowledge this is the first observation of the hypotensive effect of NAS in SHR rats. This effect did not depend on the NAS conversion into melatonin since the hypotensive action of NAS was more pronounced in pinealectomized than in sham-operated rats. The potentiation of the hypotensive effect of NAS by HIOMIT inhibitor, SAH, only in sham-operated but not in pinealectomized rats further supports our hypothesis that NAS but not melatonin caused the hypotensive effect.

Traditionally, the effects of the pineal gland are attributed to its "major" hormone, melatonin, although melatonin is not the only compound which is synthesized from serotonin in the pineal gland.

Serotonin is acetylated by the rate-limiting enzyme N-acetyltransferase (NAT) with the formation of N-acetylserotonin (NAS) which is then methylated by hydroxyindole-O-methyltransferase (HIOMT) to produce melatonin (5-methoxy-N-acetyltryptamine) (see Reiter, 1991). Serotonin and melatonin were considered as the biologically active compounds, while NAS was viewed only as an intermediate product of melatonin biosynthesis, although some authors suggested that NAS may be a hormone in its own right (Allen et al., 1991).

Until now, the hypotensive effect was attributed to melatonin (see Karppanen, 1974). It was shown that melatonin (in drinking water) prevented pinealectomy-induced hypertension in normotensive Wistar rats (Karppanen, 1974; Holmes & Sugden, 1975) and exerted slight but statistically significant hypotensive effect in SHR rats while administered subchronically (via i.p. minipumps) in very high doses (Kawasima et al., 1987). However, the acute administration of melatonin via different systemic and intraventricular routes failed to decrease blood pressure in SHR rats (Karppanen, 1974). In this regard, it is noteworthy that about 30% of melatonin is reconverted (deacetylated) to its precursor (NAS) (Leone and Silman, 1984), and, therefore, the effects (e.g., hypotensive) of the very high doses of melatonin might be attributed to NAS rather than to melatonin.

The hypotensive effect of NAS might be discussed in terms of its mechanism(s), its role in the physiological regulation of blood pressure and in the development of hypertension, and in therapeutic effect in the treatment and/or prevention of hypertension.

The mechanism(s) of the hypotensive effect of NAS are unknown. Our data indicates that this effect does not depend on the NAS transformation into melatonin. The hypotensive effect should not depend on the NAS stimulation of serotonin receptors since the likely result of such interaction would be the increase of blood pressure. One may speculate that NAS might interact with the yet unidentified NAS receptors (or binding sites).

The hypotensive effect of NAS might contribute to the circadian variation of blood pressure, i.e., its decrease during the dark phase.

Since pineal NAS production decreased with aging, one might suggest that age-associated decrease of NAS production might contribute to the age-associated increase of blood pressure. It is noteworthy that NAS production by the aged pineals could not be increased by the stimulation of NAT activity, and, therefore, administration of NAS might the important tool to increase NAS content in aged subjects. In fact, considering the demonstration of the HIOMT deficiency in aged rats, the administration of just NAS (even without HIOMT inhibitor) might be very effective in aged subjects. In the young subjects administration of NAS might be more effective if combined with the HIOMT inhibitor (e.g., SAH, but not limited to SAH), or of some NAS formulation which would allow the sustained release of NAS or some form of protection from the O-methylation into melatonin, or from other routes of metabolism.

In conclusion, our results suggested that NAS exerts hypotensive effect. This effect is attenuated by the inhibitor of NAS conversion into melatonin and by pinealectomy, i.e., this effect does not depend on NAS conversion into melatonin. It is proposed that NAS (alone or in combination with the inhibitors of NAS metabolism into melatonin) might be used for the treatment of hypertension.

The following references are cited throughout the specification. All documents mentioned herein are incorporated herein by reference.

Allen A E, Pang S F and I. Nir (1991) The effect of environmental photoperiodicity on indole rhythms and locomotor activity in sighted and eye covered chickens. J. Neural Transm, 83:107–119.

Bhattacharya, S. K., Glover, V., McIntyre, I., Oxenkrug, G., and Sandler, N I., Stress causes an increase in endogenous monoamine oxidase inhibitor (tribulin) in rat brain, Neurosci. Lettr, 92 (1988) 218–221

Bunag, R. D., and Butterfield, J., Tall-cuff blood pressure measurement without external preheating in awake rats. Hypertension, 4 (1982) 898–903

Finocchiaro L M E, Scheucher A, Alvarez A L, Finkelman S, Nahmod V E and C J Pirola (1990) Pineal hyperreactivity' in spontaneously hypertensive rats: muscarinic regulation of indole metabolism. Clinical Science, 79: 437–442

Fletcher B C, Lesske J, Culman J, Miller C C and T. Unger (1992) Sympathetic denervation blocks blood pressure elevation in episodic hypoxia. Hypertension, 20: 612–619

Haeusler G, Finch L and H. Thoenen (1972) Central adrenergic neurones and the initiation and development of experimental hypertension. Experientia, 28:1200–1203

Holmes, S. W., and Sugden, D., The effect of melatonin on pinealectomy-induced hypertension in the rat, Br.,J., Pharmacol.,55 (1975) 360P–361P Horrax G (1916) Studies on the pineal gland. Arch Inter Med, 607–625

Howell W H (1898) The physiological effects of extracts of the hypophysis cerebri and infundibulae body. J Exp Med, iii: 245–258

Illerova, H., Albrecht, I. (1975) Isoproterenol induction of pineal serotonin Nacetyltransferase in normotensive and spontaneously hypertensive rats. Experientia 31: 95

Karppanen, H. Studies on pinealectomy-induced hypertension in rats, Doctoral Thesis 1974, Helsinki.

Kawashima K., Nagakura, A., Wurzberger R. J., Spector, 5. (1984). Nlelatonin in serum and the pineal of spontaneously hypertensive rats. Clin.& Exper. Hypertension—Theory & Practice, A6(8):15517–1528

Kawashima, K., Miwa, Y., Fujimoto, K., Oohata, H., Nishino, H., and Koike, H., Antihypertensive action of melatonin in the spontaneously hypertensive rat, Clin. Exper. Hypertension—Theory and Practice, A9(7) (1987) 1121–1131

Leone R M and R E Silman( 1984) NIelatonin can be differentially metabolized in the rat to produce N-acetvl-serotonin in addition to 6-hydroxy-melatonin. Endocrinology, 114: 1825–1832

Okamoto K and K. Aoki (1963) Development of a strain of spontaneously hypertensive rats. Jpn Circ J, 27: 282–293

Oxenkrug (1991) The acute effect of monoamine oxidase inhibitors on serotonin conversion to melatonin. In: 5-Hydroxytryptamine and Mental Illness. Coppen A, Sandier NI and Harnett S (eds). Oxford Univ. Press, pp.99–108

Oxenkrug, G. F. & P. J. Requintina (1991) Phase advanced circadian rhythm of the pineal melatonin biosynthesis inspontaneously hypertensive rats. In Neurology of circadian and seasonal rhythms, P. Laudat conference INSERM p.179.

Oxenkrug, G. F., and McIntyre, I. M., Stress-induced synthesis of melatonin: possible involvement of the endogenous monoamine oxidase inhibitor (Tribulin), Life Sci. 37 (1985) 1743–1746

Oxenkrug, G. E., McCauley, R. B., Fontana, D. J., McIntyre, I. M., Commissaris, R. L., Possible melatonin involvement in the hypotensive effect of MAO inhibitors, J. Neural Transm., 66(1986) 271–280

Oxenkrug, G., McIntyre, I., McCauley, R., Filipowicz. C. Selective inhibition of MAO-A but not MAO-B activity' increases rat pineal melatonin. J. Neural Trans., 61(1985) 265–270

Reiter, R J (1991) Pineal melatonin—cell biology of its synthesis and of its physiological interaction. Endocrin. Rev., 12: 151–180

Reuss, S., & G. E. Oxenkrug (1989) Chemical sympatectomy and clorgyline-induced stimulation of rat pineal melatonin synthesis. J neural Transm, 78:167–172

Zanoboni, A., Zanoboni-Muciaccia, W., Experimental hypertension in pinealectomized rats, Life Sci., 6 (1967) 2327–2331

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method for the treatment of hypertension in a mammal in need thereof which comprises administering to said mammal a therapeutically effective antihypertensive amount of N-acetyl-serotonin (NAS) or a pharmaceutically acceptable salt thereof.

2. The method of claim 1, wherein the mammal is a human.

3. The method of claim 1, wherein said NAS is administered by the oral route.

4. The method of claim 1, wherein said NAS is administered together with an acceptable carrier therefor.

5. The method of claim 1, wherein said NAS is administered in the form of an orally ingestible capsule or tablet.

6. The method of claim 1, wherein said NAS is administered in combination with S-adenosylhomocysteine.

\* \* \* \* \*